(12) United States Patent
Smith

(10) Patent No.: US 6,656,164 B1
(45) Date of Patent: Dec. 2, 2003

(54) RETRACTABLE NEEDLE DEVICE

(75) Inventor: Mark T. Smith, London (CA)

(73) Assignee: Computer Controlled Syringe, Inc. (CA)

(*) Notice: Subject to any disclaimer, the term of this patent is extended or adjusted under 35 U.S.C. 154(b) by 41 days.

(21) Appl. No.: 10/070,502

(22) PCT Filed: Sep. 7, 2000

(86) PCT No.: PCT/CA00/01023
§ 371 (c)(1),
(2), (4) Date: Mar. 7, 2002

(87) PCT Pub. No.: WO01/17593
PCT Pub. Date: Mar. 15, 2001

Related U.S. Application Data

(60) Provisional application No. 60/152,341, filed on Sep. 7, 1999.

(51) Int. Cl.⁷ .............................. A61M 5/00; A61M 5/32
(52) U.S. Cl. ...................................... 604/232; 604/192
(58) Field of Search .............................. 604/232, 192, 604/195, 196, 198, 201, 222, 205, 215, 234, 235, 236, 110

(56) References Cited

U.S. PATENT DOCUMENTS

| 4,108,177 A |   | 8/1978  | Pistor ............................ 128/218 |
| 4,553,962 A | * | 11/1985 | Brunet .......................... 604/198 |
| 4,931,040 A | * | 6/1990  | Haber et al. .................. 604/110 |
| 5,167,641 A | * | 12/1992 | Schmitz ......................... 604/232 |
| 5,201,719 A | * | 4/1993  | Collins et al. ................. 604/195 |
| 5,279,579 A | * | 1/1994  | D'Amico ...................... 604/192 |
| 5,403,288 A | * | 4/1995  | Stanners ....................... 604/232 |
| 5,514,107 A | * | 5/1996  | Haber et al. .................. 604/197 |
| 5,522,812 A | * | 6/1996  | Talonn et al. ................. 604/198 |
| 5,634,906 A |   | 6/1997  | Haber et al. .................. 604/136 |
| 5,658,259 A |   | 8/1997  | Pearson et al. ............... 604/232 |
| 5,690,618 A |   | 11/1997 | Smith et al. ................... 604/232 |
| 5,693,023 A | * | 12/1997 | Adams .......................... 604/195 |
| 5,800,403 A | * | 9/1998  | Pressly, Sr. et al. ......... 604/195 |
| 5,810,775 A | * | 9/1998  | Shaw ............................ 604/110 |
| 5,817,064 A | * | 10/1998 | DeMarco ..................... 604/198 |
| 5,938,641 A | * | 8/1999  | Villanueva .................... 604/195 |
| 5,989,226 A | * | 11/1999 | Hymanson .................... 604/198 |
| 6,221,055 B1 | * | 4/2001 | Shaw et al. ................... 604/232 |

FOREIGN PATENT DOCUMENTS

| EP | 0516473 A1 | 12/1992 | ............ A61M/5/20 |
| FR | 2767479    | 2/1999  | ............ A61M/5/20 |
| WO | WO 99/55401 | 11/1999 | ............ A61M/5/315 |

* cited by examiner

*Primary Examiner*—Sharon Kennedy
(74) *Attorney, Agent, or Firm*—Katten Muchin Zavin Rosenman

(57) ABSTRACT

The present invention provides, in a preferred embodiment, a retractable needle (26) device for use with a syringe. The syringe may be manually driven or electronically driven. In the retracted position, the needle is enclosed within a safety shield and may be extended from the safety shield (60) upon actuation of the plunger (38) normally used to dispense the biocompatible material from the needle. In this instance, initial pressure on the plunger serves to extract the needle and after the needle is extracted, the biocompatible material is dispensed from a carpule in communication with the needle. When it is desired to retract the needle, the direction of the plunger travel is reversed thereby effectively retracting the needle back in to the safety shield.

45 Claims, 4 Drawing Sheets

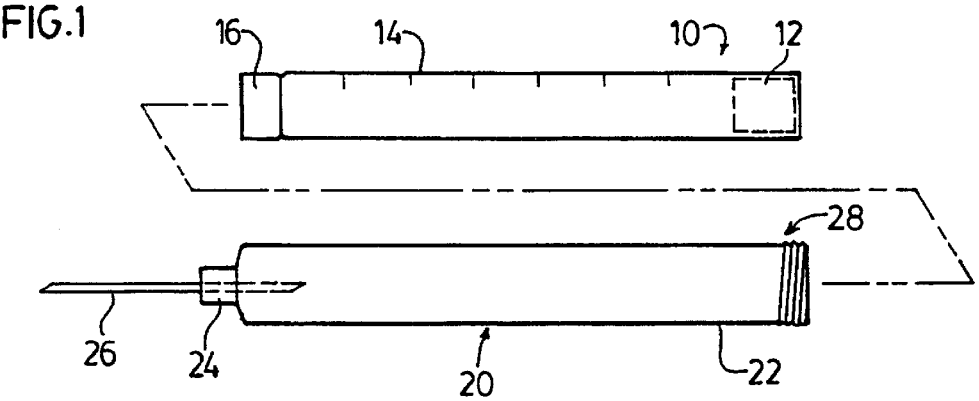
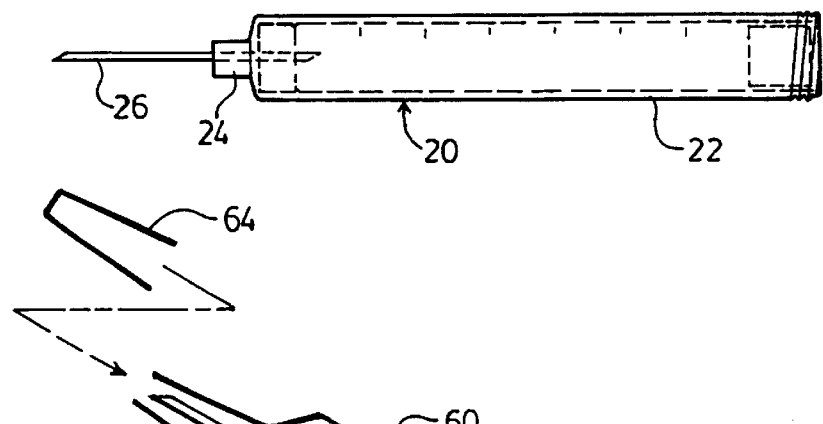
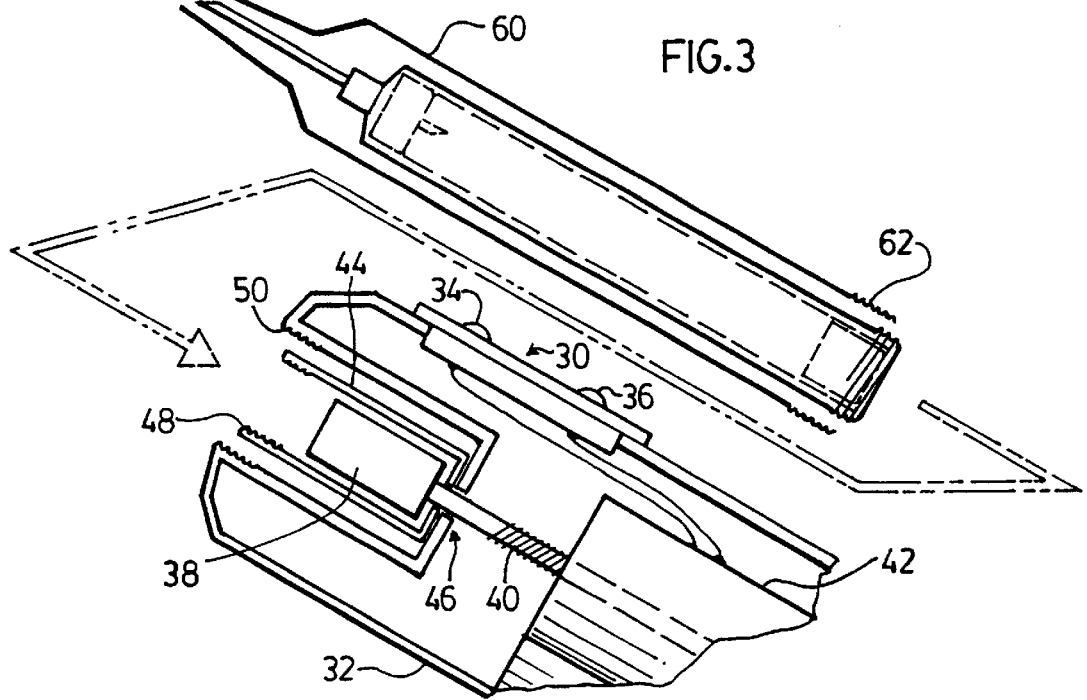

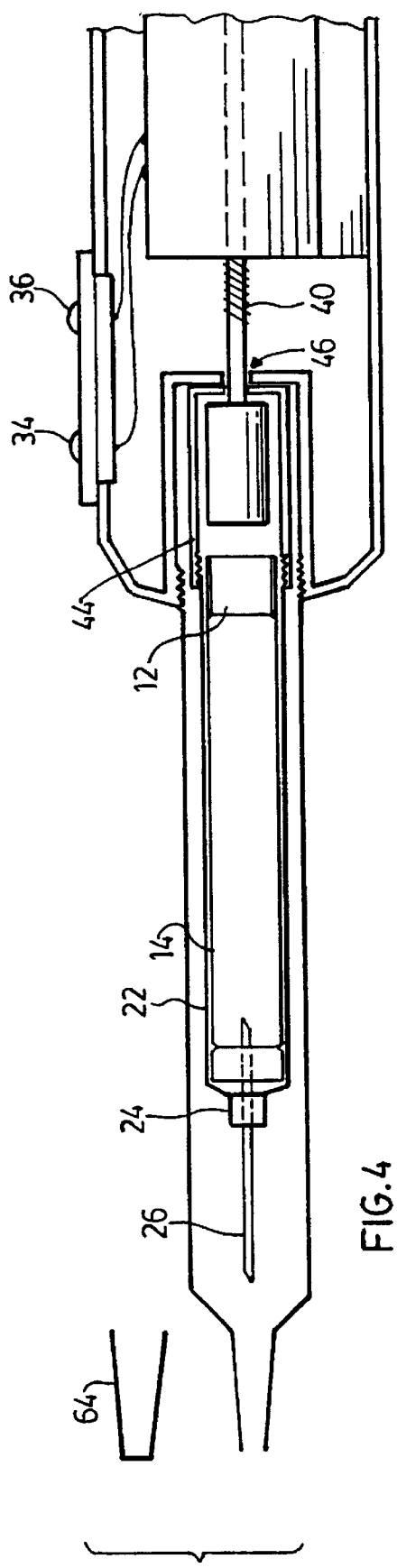
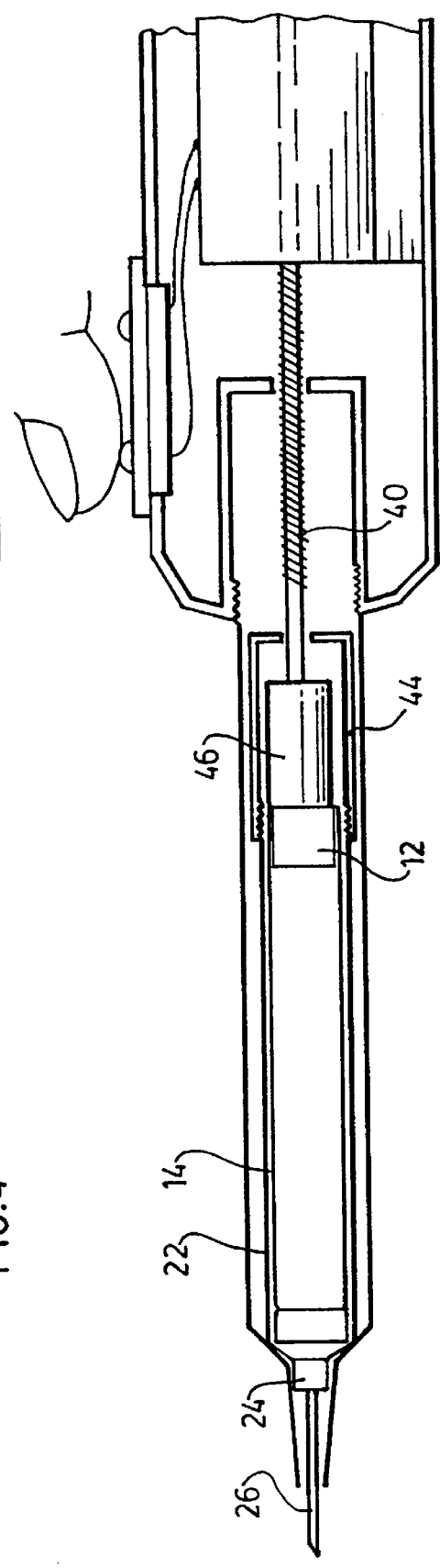
FIG.4
FIG.5

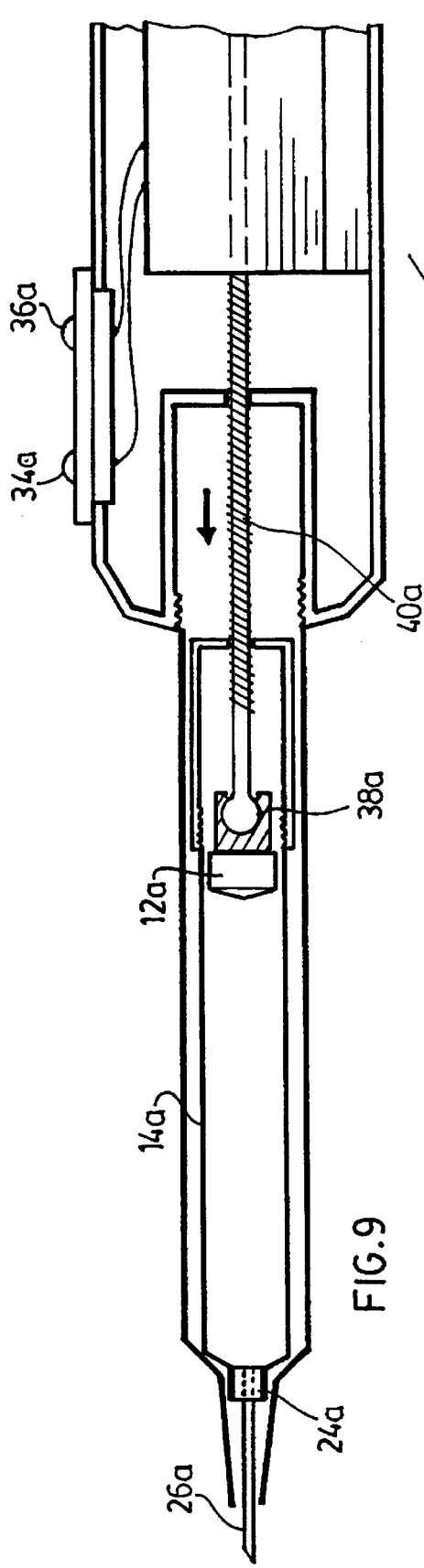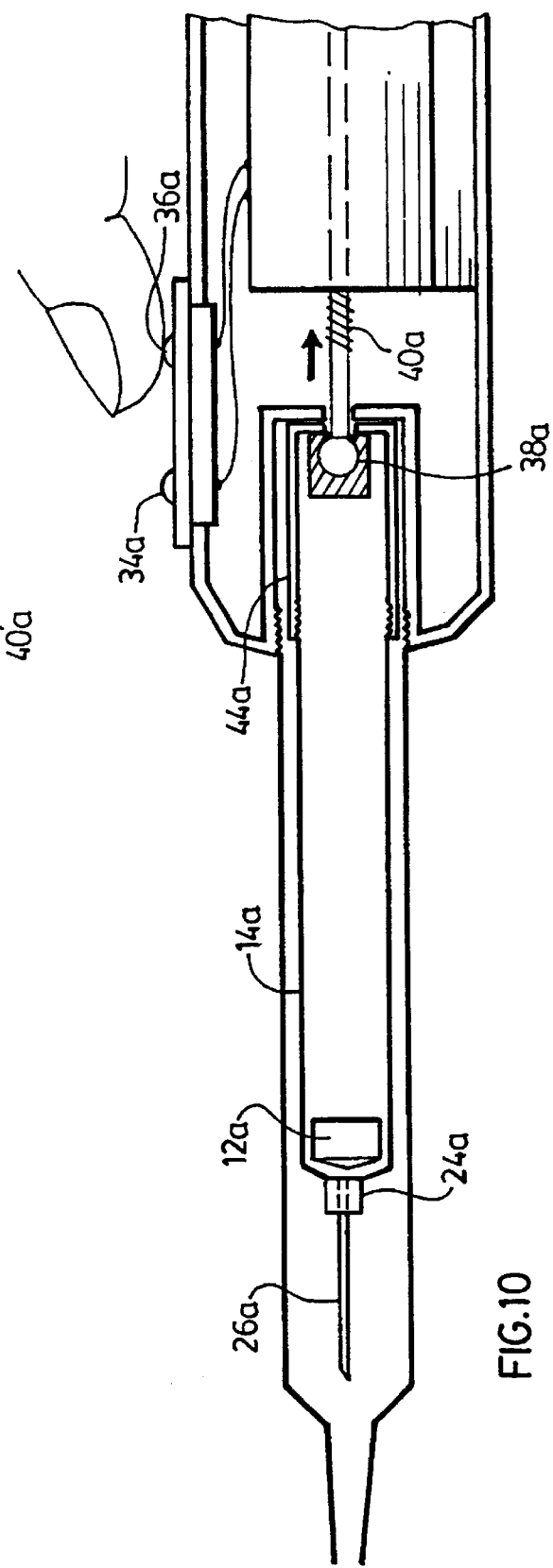
FIG.9
FIG.10

RETRACTABLE NEEDLE DEVICE

This application claims the benefit of U.S. provisional application No. 60/152,341, filed Sep. 7, 1999.

TECHNICAL FIELD

In one of its aspects, the present invention relates to a retractable needle device. In another of its aspects, the present invention relates to syringe comprising a retractable needle device.

BACKGROUND ART

Syringes are generally known.

One class of syringes are manual syringes in which the user actuates pressure on the contents of the syringe thereby dispensing the medicant or other material to be injected to a patient.

Electronic syringes are known in the art. Typical uses for such devices include injecting biocompatible material, specifically anaesthetics such as block, conduction and para-apicalanaesthesia, through bone tissue and administering insulin and other pharmaceuticals.

In most dental applications, practitioners are required to regularly administer anaesthetic injections in confined spaces using conventional manual syringes.

Conventional manual syringes, as used in dentistry applications, usually comprise a hollow cylindrical housing having one end adapted to receive a needle and the other end adapted to receive a piston assembly. The outer surface of the housing is provided with a pair of finger grips such that the device can be held firmly between the middle and index fingers of the practitioner's hand. Anaesthetic is commonly supplied in premeasured ampules which are designed to fit in to the housing. The ampule has one end provided with a pierceable membrane that receives a proximal end of the needle in sealing engagement and another end fitted with a slidable stopper which engages a distal end of the piston assembly. The piston assembly includes a shaft, which is fitted with a plunger at its distal end and a thumb rest at its proximal end. In operation, the anaesthetic injection is administered by depressing the plunger with the practitioner's thumb which causes the piston assembly to engage and push the stopper, thereby forcing anaesthetic from the ampule via the needle.

Many of the difficulties associated with manual syringes have been obviated and/or mitigated by the teachings of U.S. Pat. No. 5,690,618 [Smith] and International publication number WO 99/55401 [Smith et al.]. These innovations relate to improving the safety of the syringe device by reducing patient discomfort and fear of the syringes.

Despite these improvements, there is an ongoing need to improve the safety of syringe devices generally.

One of the ongoing safety issues is inadvertent "sticking" of the practitioner and/or the patient by an exposed needle. While the needle in conventional syringes typically come with removable caps or sleeves, it would be desirable to have a system in which the needle would automatically extend for injection and retract after injection upon actuation of the plunger normally used to inject the biocompatible material.

DISCLOSURE OF THE INVENTION

It is an object of the present invention to provide a novel retractable needle device which obviates or mitigates at least one of the above-mentioned disadvantages of the prior art.

Accordingly, in one of its aspects, the present invention provides a retractable needle device comprising:

a housing comprising a plunger operable between a first, extended position and a first, retracted position;

a shield portion engaged to the housing, the shield portion comprising a first chamber;

a carpule retraction portion in sliding engagement with plunger, a carpule releaseably engaged to the carpule retraction portion, the carpule comprising a needle portion, a stopper portion and a second chamber disposed therebetween for receiving an injectable fluid, the carpule being disposed in the first chamber and being movable between a second, extended position in which the needle extends from the shield portion and a second, retracted position in which the needle is contained in the shield portion.

In another of its aspects, the present invention provides a retractable needle device comprising:

a syringe component having an outer housing, a plunger, a plunger driver connected to said plunger and operable to move said plunger between extended and retracted positions, and a secondary carpule housing in sliding communication with said plunger driver;

a safety shield releaseably engageable with said outer housing of said syringe component;

a carpule for containing said biocompatible material, the carpule having a housing with an attached needle, said carpule housing releaseably engageable with said secondary carpule housing of said syringe component, said carpule having an extracted position in which an end portion of said needle extends from said safety shield, and a retracted position in which said needle is contained within said safety shield, when said carpule housing is engaged with said secondary carpule housing and said safety shield is engaged with said outer housing, wherein when said plunger is moved to the extended position said carpule is moved to the extracted position thereby extending said needle and expelling said biocompatible material, and when said plunger is moved to the retracted position said carpule is moved to the retracted position thereby containing said needle in said safety shield.

In yet another of its aspects, the present invention provides a safety needle device for use with a syringe component, the syringe component having an outer housing, a plunger with a plunger driver connected thereto, said plunger driver operable to move said plunger between extended and retracted positions, and a secondary carpule housing in sliding communication with said plunger driver, said safety needle device having:

a safety shield releaseably engageable with said outer housing of said syringe component;

a carpule for containing said biocompatible material, the carpule having a housing having an attached needle, said carpule housing releaseably engageable with said secondary carpule housing of said syringe component, said carpule having an extracted position in which an end portion of said needle extends from said safety shield, and a retracted position in which said needle is contained within said safety shield, when said carpule housing is engaged with said secondary carpule housing and said safety shield is engaged with said outer housing, wherein when said plunger is moved to the extended position said carpule is moved to the extracted position thereby extending said needle and expelling said biocompatible material, and when said plunger is moved to the retracted position said carpule is moved to the retracted position thereby containing said needle in said safety shield.

In yet another of its aspects, the present invention provides a retractable needle device for use with a carpule containing a biocompatible material, said device having:

a syringe component having an outer housing, a plunger with a plunger driver connected thereto, said plunger driver operable to move said plunger between extended and retracted positions, and a secondary carpule housing in sliding communication with said plunger driver;

a safety shield releaseably engageable with said outer housing of said syringe component;

a carpule housing having an attached needle, for receiving said carpule, said carpule housing releaseably engageable with said secondary carpule housing of said syringe component, said carpule housing having an extracted position in which an end portion of said needle extends from said safety shield, and a retracted position in which said needle is contained within said safety shield, when said carpule housing is engaged with said secondary carpule housing and said safety shield is engaged with said outer housing, wherein when said plunger is moved to the extended position said carpule housing is moved to the extracted position thereby extending said needle and expelling said biocompatible material, and when said plunger is moved to the retracted position said carpule housing is moved to the retracted position thereby containing said needle in said safety shield.

In yet another of its aspects, the present invention provides a safety needle device for use with a carpule containing a biocompatible material and a syringe component having an outer housing, a plunger with a plunger driver connected thereto, said plunger driver operable to move said plunger between extended and retracted positions, and a secondary carpule housing in sliding communication with said plunger driver, said safety needle device having:

a safety shield releaseably engageable with said outer housing of said syringe component;

a carpule housing having an attached needle, for receiving said carpule, said carpule housing releaseably engageable with said secondary carpule housing of said syringe component, said carpule housing having an extracted position in which an end portion of said needle extends from said safety shield, and a retracted position in which said needle is contained within said safety shield, when said carpule housing is engaged with said secondary carpule housing and said safety shield is engaged with said outer housing, wherein when said plunger is moved to the extended position said carpule housing is moved to the extracted position thereby extending said needle and expelling said biocompatible material, and when said plunger is moved to the retracted position said carpule housing is moved to the retracted position thereby containing said needle in said safety shield.

Thus, in one of its aspects, the present invention provides a retractable needle device for use with a syringe. The syringe may be manually driven or electronically driven. In the retracted position, the needle is enclosed within a safety shield and may be extended from the safety shield upon actuation of the plunger normally used to dispense the biocompatible material from the needle. In this instance, initial pressure on the plunger serves to extract the needle and after the needle is extracted, the biocompatible material is dispensed from a carpule in communication with the needle. When it is desired to retract the needle, the direction of the plunger travel is reversed thereby effectively retracting the needle back in to the safety shield.

BRIEF DESCRIPTION OF THE DRAWINGS

Embodiments of the present invention will be described with reference to the accompanying drawings wherein like numerals designate like elements and in which:

FIGS. 1 and 2 illustrate perspective views, in partial cross-section, of a carpule and carpule housing useful in a preferred embodiment of the present retractable needle device;

FIG. 3 illustrates a perspective view, in partial cross-section, of attachment of the carpule housing illustrated in FIGS. 1 and 2 to an electronic syringe device;

FIGS. 4 and 5 illustrate perspective views, in partial cross-section, of use of the syringe device illustrated in FIG. 3; and FIGS. 6–10 illustrate an alternate embodiment wherein the independent carpule and carpule housing elements in FIGS. 1–5 are replaced with an integral carpule/housing unit.

BEST MODE FOR CARRYING OUT THE INVENTION

Figure 6:
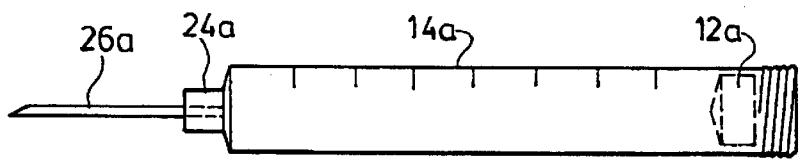

With reference to the accompanying drawings, specific preferred embodiments of the present invention will be described.

Thus, with reference to FIG. 1, there is illustrated a carpule 10 comprising a rubber stopper 12 slidable within a housing 14. Disposed at the opposite end of rubber stopper 12 is a rubber gasket 16.

Carpule 10 may be disposed in a carpule housing 20 which comprises a sleeve 22, a head 24, a needle 26 disposed within head 24 and a threaded outer surface 28. When carpule 10 is disposed within carpule housing 20 and pushed all the way in, the proximal end of needle 26 in carpule housing 20 pierces rubber gasket 16 of carpule 10. The combined unit of carpule 10 and carpule housing 20 is illustrated in FIG. 2.

Figure 7:
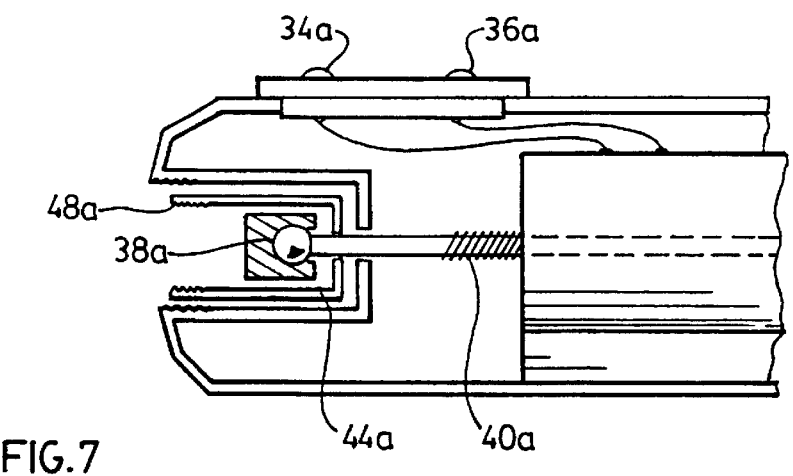
Figure 8:
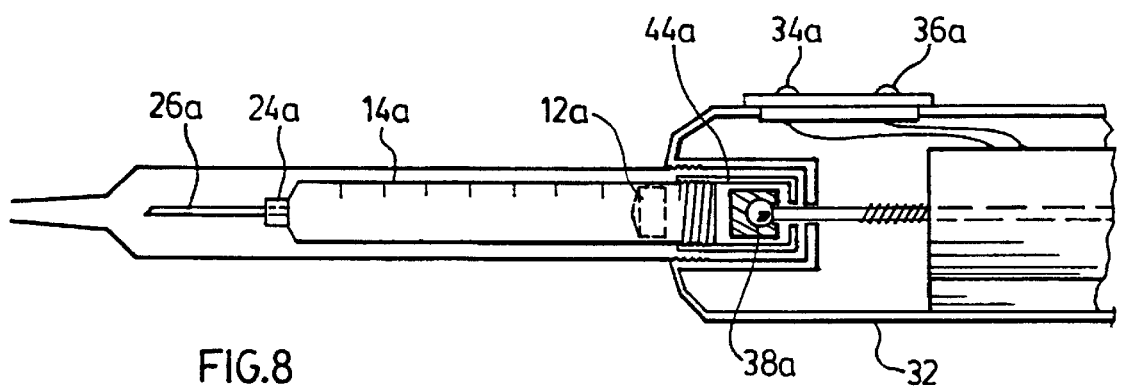

Alternatively, carpule 10 and carpule housing 20 may be replaced with an integral carpule/housing unit. This is especially useful in medical applications of the syringe—see FIGS. 6–10 referred to hereinbelow.

With reference to FIG. 3, there is illustrated a distal end 30 of an electronic syringe of similar design to the one taught in U.S. Pat. No. 5,690,618 [Smith] and International publication number WO 99/55401 [Smith et al.] referred to hereinabove. Distal end 30 comprises a housing 32 having located on the outside thereof the forward switch 34 and a reverse switch 36. Disposed within housing 32 is a plunger 38 connected to a lead screw 40 which, in turn, is connected to an electronic motor 42.

Also disposed within housing 32 is a secondary carpule housing 44. As illustrated, a spacing 46 is provided between lead screw 40 and secondary carpule housing 44 allowing the latter (in combination with plunger 38) to extend and retract with respect to the former. The design of the remainder of the electronic syringe preferably is as described in U.S. Pat. No. 5,690,618 [Smith] and International publication number WO 99/55401 [Smith et al.] referred to hereinabove.

Secondary carpule housing 44 comprises an internally threaded portion 48 for engagement with threaded outer surface 28 of carpule housing 20. On the interior surface of housing 32 are located a first pair of locking lugs 50.

Disposed distally of housing 30 is a safety shield 60. The proximal end of safety shield 60 comprises a second pair of locking lugs 62. First pair of locking lugs 50 and second pair of locking lugs 62 are designed in a conventional manner to achieve reversible engagement housing 30 and safety shield 60. A cap 64 is provided for removably covering the distal end of safety shield 60.

The combined carpule/carpule housing illustrated in FIG. 2 may then be disposed in safety shield 60 and the latter may be locked with respect to distal end 30 of the electronic syringe—this is illustrated in FIG. 4. As shown in FIG. 4, needle 26 is in the retracted, passive state in which it is fully enclosed within safety shield 60.

When it is desired to inject a biocompatible material, forward switch 34 in housing 32 is actuated. This drives motor 42 which results in extension of lead screw 40 and plunger 38. Plunger 38 abuts rubber stopper 12. The respective dimensions of carpule housing 20 and safety shield 60 are selected so that the linear force necessary to overcome friction between the two elements is less than the force required to move rubber stopper 12—i.e., avoiding premature dispensing of the biocompatible material. This results in movement of the entire carpule/carpule housing combination within safety shield 60 until head 24 abuts against the tapered portion near the distal end of interior of safety shield 60—this is shown in FIG. 5. At this point, needle 26 is extended from safety shield 60 and continued application of linear force by plunger 38 results in movement of rubber stopper 12 thereby injecting biocompatible material from the now exposed needle 26.

When it is desired to retract needle 26, reverse switch 36 on distal end 30 of the electronic syringe is actuated thereby reversing the direction of motor 40. This results in reversal of the direction of lead screw 40 and retraction of plunger 38. Once plunger 38 abuts the proximal end of secondary carpule housing 44, the unit of secondary carpule housing 44 and carpule housing 20 is retracted toward housing 32 whereby the needle is retracted within safety shield 60 as shown in FIG. 4.

FIGS. 6–10 illustrate an alternate embodiment of the present invention where an integral carpule/carpule housing is used (as referred to hereinabove). Preferably, the integral carpule/carpule housing is pre-filled with the biocompatible or injectable fluid of interest. In FIGS. 6–10, the suffix "a" has been added to each reference numeral to denote like elements to the embodiment illustrated in FIGS. 1–5. The operation of the alternate embodiment shown in FIGS. 6–10 is similar to the one shown in FIGS. 1–5.

While the present invention has been described with reference to preferred and specifically illustrated embodiments, it will of course be understood by those skilled in the arts that various modifications to these preferred and illustrated embodiments may be made without the parting from the spirit and scope of the invention.

All publications, patents and patent applications referred to herein are incorporated by reference in their entirety to the same extent as if each individual publication, patent or patent application was specifically and individually indicated to be incorporated by reference in its entirety.

What is claimed is:

1. A retractable needle device comprising:
    a housing comprising a plunger operable between a first, extended position and a first, retracted position;
    a shield portion engaged to the housing, the shield portion comprising a first chamber,
    a carpule retraction portion in sliding engagement with plunger,
    a carpule releaseably engaged to the carpule retraction portion, the carpule comprising a needle portion, a stopper portion and a second chamber disposed therebetween for receiving an injectable fluid, the carpule being disposed in the first chamber and being movable between a second, extended position in which the needle extends from the shield portion and a second, retracted position in which the needle is contained in the shield portion.

2. The device defined in claim 1, wherein the carpule is movable to the second, extended position by urging the plunger against the stopper.

3. The device defined in claim 1, wherein the carpule is movable to the second, retracted position by urging the plunger against the carpule retraction portion.

4. The device defined in claim 1, further comprising motive means connect to the plunger to move the plunger between the first, extended position and the first, retracted position.

5. The device defined in claim 1, further comprising electric motive means connect to the plunger to move the plunger between the first, extended position and the first, retracted position.

6. The device defined in claim 1, wherein the carpule comprises a carpule housing and a carpule barrel.

7. The device defined in claim 6, wherein the carpule housing comprises the needle.

8. The device defined in claim 6, wherein the carpule barrel comprises the stopper portion.

9. The device defined in claim 6, wherein the carpule barrel further comprises a pierceable portion which is pierced by a proximal end of the needle upon combination of the carpule barrel and the carpule housing.

10. A retractable needle device comprising:
    a syringe component having an outer housing, a plunger, a plunger driver connected to said plunger and operable to move said plunger between extended and retracted positions, and a secondary carpule housing in sliding communication with said plunger driver;
    a safety shield releaseably engageable with said outer housing of said syringe component;
    a carpule for containing said biocompatible material, the carpule having a housing with an attached needle, said carpule housing releaseably engageable with said secondary carpule housing of said syringe component, said carpule having an extracted position in which an end portion of said needle extends from said safety shield, and a retracted position in which said needle is contained within said safety shield, when said carpule housing is engaged with said secondary carpule housing and said safety shield is engaged with said outer housing,
    wherein when said plunger is moved to the extended position said carpule is moved to the extracted position thereby extending said needle and expelling said biocompatible material, and when said plunger is moved to the retracted position said carpule is moved to the retracted position thereby containing said needle in said safety shield.

11. The device defined in claim 10, wherein said syringe component is an electronic syringe component.

12. The device defined in claim 10, wherein said syringe component is manually operated.

13. The device defined in claim 10, wherein said carpule is integral with said carpule housing.

14. The device defined in claim 10, wherein said carpule is disposed in said carpule housing.

15. The device defined in claim 10, wherein said outer housing of said syringe component has a pair of locking lugs on an interior surface and said safety shield has a complementary pair of locking lugs at a proximal end, said complementary locking lugs for releaseable engagement with said locking lugs.

16. The device defined in claim 14, wherein said secondary carpule housing has an internally threaded portion and said carpule housing has a threaded outer portion, said threaded outer portion for releaseable engagement with said internally threaded portion.

17. The device defined in claim 12, wherein said plunger driver comprises a lead screw.

18. The device defined in claim 11, wherein said electronic syringe component also has a forward switch for moving said plunger to the extended position, and a reverse switch for moving said plunger to the retracted position.

19. The device defined in claim 11, wherein said carpule has a sleeve, a stopper at a first end os said sleeve and slidable therein, and a gasket at an opposing end of said sleeve.

20. The device defined in claim 19, wherein when said plunger is moved from the retracted to the extended position, said plunger abuts said stopper of said carpule, thereby extending said needle, sliding said stopper in said sleeve and expressing said biocompatible material.

21. The device defined in claim 20, wherein when said plunger is moved from the extended to the retracted position, said plunger abuts said secondary carpule housing thereby retracting said carpule housing and said needle.

22. A safety needle device for use with a syringe component, the syringe component having an outer housing, a plunger with a plunger driver connected thereto, said plunger driver operable to move said plunger between extended and retracted positions, and a secondary carpule housing in sliding communication with said plunger driver, said safety needle device having:
   a safety shield releaseably engageable with said outer housing of said syringe component;
   a carpule for containing said biocompatible material, the carpule having a housing having an attached needle, said carpule housing releaseably engageable with said secondary carpule housing of said syringe component, said carpule having an extracted position in which an end portion of said needle extends from said safety shield, and a retracted position in which said needle is contained within said safety shield, when said carpule housing is engaged with said secondary carpule housing and said safety shield is engaged with said outer housing,
   wherein when said plunger is moved to the extended position said carpule is moved to the extracted position thereby extending said needle and expelling said biocompatible material, and when said plunger is moved to the retracted position said carpule is moved to the retracted position thereby containing said needle in said safety shield.

23. The device defined in claim 22, wherein said syringe component is an electronic syringe component.

24. The device defined in claim 22, wherein said syringe component is manually operated.

25. The device defined in claim 22, wherein said carpule is integral with said carpule housing.

26. The device defined in claim 22, wherein said carpule is disposed in said carpule housing.

27. The device defined in claim 22, wherein said safety shield has a pair of locking lugs on a proximal end for releaseable engagement with a pair of complementary locking lugs on said outer housing of said syringe component.

28. The device defined in claim 26, wherein said carpule housing has a threaded outer portion for releaseable engagement with an internally threaded portion of said secondary carpule housing.

29. The device defined in claim 22, wherein said carpule has a sleeve, a stopper at a first end of said sleeve and slidable therein, and a gasket at an opposing end of said sleeve.

30. The device defined in claim 29, wherein when said plunger is moved from the retracted to the extended position, said plunger abuts said stopper of said carpule, thereby extending said needle, sliding said stopper in said sleeve and expressing said biocompatible material.

31. The device defined in claim 30, wherein when said plunger is moved from the extended to the retracted position, said plunger abuts said secondary carpule housing thereby retracting said carpule housing and said needle.

32. A retractable needle device for use with a carpule containing a biocompatible material, said device having:
   a syringe component having an outer housing, a plunger with a plunger driver connected thereto, said plunger driver operable to move said plunger between extended and retracted positions, and a secondary carpule housing in sliding communication with said plunger driver;
   a safety shield releaseably engageable with said outer housing of said syringe component;
   a carpule housing having an attached needle, for receiving said carpule, said carpule housing releaseably engageable with said secondary carpule housing of said syringe component, said carpule housing having an extracted position in which an end portion of said needle extends from said safety shield, and a retracted position in which said needle is contained within said safety shield, when said carpule housing is engaged with said secondary carpule housing and said safety shield is engaged with said outer housing;
   wherein when said plunger is moved to the extended position said carpule housing is moved to the extracted position thereby extending said needle and expelling said biocompatible material, and when said plunger is moved to the retracted position said carpule housing is moved to the retracted position thereby containing said needle in said safety shield.

33. The device defined in claim 32, wherein said syringe component is an electronic syringe component.

34. The device defined in claim 32, wherein said syringe component is manually operated.

35. The device defined in claim 32, wherein said outer housing of said syringe component has a pair of locking lugs on an interior surface and said safety shield has a complementary pair of locking lugs at a proximal end, said complementary locking lugs for releaseable engagement with said locking lugs.

36. The device defined in claim 32, wherein said secondary carpule housing has an internally threaded portion and said carpule housing has a threaded outer portion, said threaded outer portion for releaseable engagement with said internally threaded portion.

37. The device defined in claim 33, wherein said plunger driver comprises a lead screw.

38. The device defined in claim 37, wherein said electronic syringe component also has a forward switch for moving said plunger to the extended position, and a reverse switch for moving said plunger to the retracted position.

39. The device defined in claim 32, wherein when said plunger is moved from the retracted to the extended position, said plunger abuts said carpule, thereby extending said needle and expressing said biocompatible material.

40. The device defined in claim 39, wherein when said plunger is moved from the extended to the retracted position, said plunger abuts said secondary carpule housing thereby retracting said carpule housing and said needle.

41. A safety needle device for use with a carpule containing a biocompatible material and a syringe component having an outer housing, a plunger with a plunger driver connected thereto, said plunger driver operable to move said plunger between extended and retracted positions, and a secondary carpule housing in sliding communication with said plunger driver, said safety needle device having:

a safety shield releaseably engageable with said outer housing of said syringe component;

a carpule housing having an attached needle, for receiving said carpule, said carpule housing releaseably engageable with said secondary carpule housing of said syringe component, said carpule housing having an extracted position in which an end portion of said needle extends from said safety shield, and a retracted position in which said needle is contained within said safety shield, when said carpule housing is engaged with said secondary carpule housing and said safety shield is engaged with said outer housing;

wherein when said plunger is moved to the extended position said carpule housing is moved to the extracted position thereby extending said needle and expelling said biocompatible material, and when said plunger is moved to the retracted position said carpule housing is moved to the retracted position thereby containing said needle in said safety shield.

42. The device defined in claim 41, wherein said syringe component is an electronic syringe component.

43. The device defined in claim 41, wherein said syringe component is manually operated.

44. The device defined in claim 41, wherein said safety shield has a pair of locking lugs on a proximal end for releaseable engagement with a pair of complementary locking lugs on said outer housing of said syringe component.

45. The device defined in claims 41, wherein said carpule housing has a threaded outer portion for releaseable engagement with an internally threaded portion of said secondary carpule housing.

* * * * *